(12) United States Patent
Dabney

(10) Patent No.: US 10,906,829 B1
(45) Date of Patent: Feb. 2, 2021

(54) LYSING OF ORGANIC MATTER WITH AUGMENTED OXIDIZING AGENTS CREATING A SOLUTION WITH REDUCED MICROBIAL CONCENTRATION

(71) Applicant: EMODs Technology, L.L.C., Georgetown, TX (US)

(72) Inventor: Paul Dabney, Georgetown, TX (US)

(73) Assignee: EMODs Technology, L.L.C., Georgetown, TX (US)

( * ) Notice: Subject to any disclaimer, the term of this patent is extended or adjusted under 35 U.S.C. 154(b) by 0 days.

(21) Appl. No.: 15/931,813

(22) Filed: May 14, 2020

(51) Int. Cl.

| | | |
|---|---|---|
| *B01D 21/00* | (2006.01) | |
| *B01D 21/01* | (2006.01) | |
| *B01D 21/26* | (2006.01) | |
| *C02F 1/02* | (2006.01) | |
| *C02F 1/32* | (2006.01) | |
| *C02F 1/38* | (2006.01) | |
| *C02F 1/66* | (2006.01) | |
| *C02F 1/72* | (2006.01) | |
| *C02F 1/78* | (2006.01) | |
| *C02F 9/00* | (2006.01) | |
| *C02F 1/76* | (2006.01) | |
| *C02F 103/00* | (2006.01) | |
| *C02F 101/30* | (2006.01) | |

(52) U.S. Cl.
CPC ............ *C02F 9/00* (2013.01); *B01D 21/0012* (2013.01); *B01D 21/01* (2013.01); *B01D 21/262* (2013.01); *C02F 1/02* (2013.01); *C02F 1/32* (2013.01); *C02F 1/38* (2013.01); *C02F 1/722* (2013.01); *C02F 1/76* (2013.01); *C02F 1/78* (2013.01); *B01D 21/009* (2013.01); *C02F 1/66* (2013.01); *C02F 2101/30* (2013.01); *C02F 2103/003* (2013.01); *C02F 2103/006* (2013.01); *C02F 2303/04* (2013.01); *C02F 2305/02* (2013.01)

(58) Field of Classification Search
CPC .. B01D 21/0012; B01D 21/009; B01D 21/01; B01D 21/262; C02F 1/02; C02F 1/32; C02F 1/38; C02F 1/66; C02F 1/722; C02F 1/76; C02F 1/78; C02F 9/00; C02F 2101/30; C02F 2103/003; C02F 2103/006; C02F 2303/04; C02F 2305/02
See application file for complete search history.

(56) References Cited

U.S. PATENT DOCUMENTS

| | | | | |
|---|---|---|---|---|
| 6,096,219 | A * | 8/2000 | Green ................. | C02F 1/325 210/173 |
| 6,623,643 | B2 * | 9/2003 | Chisholm ............. | C02F 9/00 210/620 |
| 2013/0023448 | A1 * | 1/2013 | Glasscott ............. | C02F 1/32 507/100 |
| 2015/0275166 | A1 * | 10/2015 | Feris .................... | C02F 1/32 435/257.3 |

* cited by examiner

*Primary Examiner* — Lucas A Stelling
(74) *Attorney, Agent, or Firm* — Maier & Maier, PLLC

(57) ABSTRACT

Described herein is a method for differentially lysing a liquid sample or target material using an Augmented Oxidizing Agent (AOA), which includes a quantity of Electronically Modified Oxygen Derivatives (EMODs). The method reduces or eliminates total dissolved solids (TDS), total suspended solids (TSS), microbial concentration, biofilms and other content in the liquid target material known or suspected to contain animal fluids, blood and blood cells and suspected or known to contain eukaryotic cells, microbial cells, bacteria, viruses, spores, fungi, prions, organic matter, minerals, proteins or associated structures. The TDS and TSS can be lowered or eliminated as desired. This action is directly proportional to the quantity of EMODs in the AOS applied to the liquid target material.

16 Claims, No Drawings

LYSING OF ORGANIC MATTER WITH AUGMENTED OXIDIZING AGENTS CREATING A SOLUTION WITH REDUCED MICROBIAL CONCENTRATION

BACKGROUND

Blood cells contain a dramatic amount of proteins, fats, minerals, elements and small molecular weight constituents that once separated allow disposal or repurposing of the resultant liquid in environmentally sound methods. This is one of the major reasons why, for example, blood plasma (often simply referred to as plasma, i.e. an anticoagulated whole blood sample; deprived of cells and erythrocytes) and blood serum (often simply referred to as serum, i.e. coagulated whole blood; deprived of cells, erythrocytes and most proteins of the coagulation system, especially of fibrin/fibrinogen), respectively, are used for their water value or disposed as waste. Animal Fluids, blood, blood cells, microbes, and organic matter tend to be more difficult to dispose of as compared to serum or plasma. Blood, for example, tends to be less stable and contain total dissolved solids (TDS), total suspended solids (TSS), and other components that complicate its disposal unless it is lysed. Organic matter pertains to any carbon-based compound that exists in nature. Living things are described as organic since they are composed of organic compounds. Examples of organic compounds are carbohydrates, lipids, proteins and nucleic acids. Since they are comprised of carbon-based compounds, they are broken down into smaller, simpler compounds through decomposition and through lysing. Living organisms also excrete or secrete material that is considered an organic material. The organic matter from blood may contain useful substances that contribute a value when separated from the blood. This organic matter contains substances that can be repurposed as food sources, as fertilizer, as medicines or and other uses.

At present it appears that appropriate separation/handling of animal fluids, blood, blood cells, microbes and organic matter, e.g. by centrifugation, filtration, heating, cooling, precipitation or analyte extraction is essential, before such processed sample can be properly and reliably disposed of or repurposed.

As indicated above, serum or plasma may be obtained from whole blood and repurposed or disposed of as needed. Cells, cell constituents, microbes, organic matter and erythrocytes may also be removed by filtration or centrifugation from blood or blood components or from other animal fluids but a lower cost method is desired over present commercially available techniques.

In a further way of sample processing, the animal fluids, blood, blood cells, microbes and other organic matter of interest can first separated from the majority of substances by selective precipitation or extraction methods. Extraction can be performed in liquid phase or on a solid phase. Gross extraction of larger particles can be sequenced with extraction methods progressively smaller until the desired resolution is obtained.

Debris and precipitated proteins usually are removed from a sample by centrifugation, offline filtration or solid phase extraction.

Solid phase extraction (SPE) is a technique which is used for pre-concentration and cleanup of animal fluids and blood samples, for purification of various samples, and for removal of valuable substances from aqueous solutions of animal fluids, blood microbes, and organic matter.

Erythrocytes comprised in a whole blood sample are lysed and the hemoglobin is released. The references available to the inventors of the present invention neither disclose nor suggest that a hemolysed blood sample currently can be economically prepared so that the TDS, TSS and other constituents can be separated for commercial use.

It becomes obvious from the above discussion of the state of the art that no method for a thorough, lysing, decontamination and separation of blood components exists or is available on a commercial scale that is also economically feasible. It would, however, be highly desirable if animal fluids, blood, blood cells, microbes and organic matter could be separated into useful components. This would be especially advantageous where animal fluids, blood and other liquids could be repurposed in areas where liquids are needed for animal consumption or agricultural uses are desired.

SUMMARY

The invention relates to a method for differentially lysing animal fluids, blood, blood cells, microbes, and organic matter using an Augmented Oxidizing Agent (AOA), which includes an effective amount of Electronically Modified Oxygen Derivatives (EMODs). The invention also provides for reducing or eliminating total dissolved solids (TDS), total suspended solids (TSS), microbial concentration, biofilms and other content in a liquid sample or target material, which is known or suspected to contain animal fluids, blood and blood cells and suspected or known to contain eukaryotic cells, microbial cells, organic matter, minerals, proteins or associated structures. TDS and TSS and be lowered or eliminated as desired. This action is directly proportional to the amount of EMODs applied to the blood.

The method including the steps of processing the sample or target material with a membrane solubilizing agent under conditions appropriate to lyse cell membranes of animal fluids, blood, blood cells, microbial cells or associated structures and at the same time not to cause or to cause precipitation of sample constituents, based on the desired outcome. In some instances, the precipitation of the blood constituents will be undesired because the blood and its components will be discarded. Blood with a TDS content low enough can be released into public sewer systems. At other times, the precipitation of blood components will be desired because these components are marketable as animal feed, plant fertilizer and other commodities. The lysis of blood, blood cells, microbial cells and associated structures is an advantage in a method of separating liquids and non-liquids in blood. The solubilization of blood cells can be easily combined with techniques to separate blood components as needed for various applications.

DETAILED DESCRIPTION

Aspects of the present invention are disclosed in the following detailed description. Those skilled in the art will recognize that alternative exemplary embodiments may be devised without departing from the spirit or the scope of the claims. Additionally, well-known elements of exemplary embodiments of the invention will not be described in detail or will be omitted so as not to obscure the relevant details of the invention.

As used herein, the word "exemplary" means "serving as an example, instance or illustration." The embodiments described herein are not limiting, but rather are exemplary only. It should be understood that the described embodiments are not necessarily to be construed as preferred or advantageous over other embodiments. Moreover, the terms "embodiments of the invention", "embodiments" or "invention" do not require that all embodiments of the invention include the discussed feature, advantage, or mode of operation.

Unless defined otherwise, all technical and scientific terms used herein have the meaning commonly understood by a person skilled in the art to which this disclosure belongs. The following terms may have meanings ascribed to them below, unless specified expressly otherwise. However, it should be understood that other meanings that are known or understood by those having ordinary skills in the art are also possible, and within the scope of the present disclosure.

As used herein, "organic matter" pertains to any carbon-based compound that exists in nature, non-living or living. Organic matter may consist of animal carcasses, bones, tendons, features, skin, organs, beaks, feet, hooves, snouts, or any part of animals, as well as leaves, twigs, etc. Slaughtered animals consist of organic matter but exogenous organic matter may also be incorporated into samples to be lysed. Living things are described as organic since they are composed of organic compounds. Examples of organic compounds are carbohydrates, lipids, proteins and nucleic acids. Since they are comprised of carbon-based compounds, they are broken down into smaller, simpler compounds through decomposition and through lysing. Living organisms also excrete or secrete material that is considered an organic material. Organic matter may consist of microbes and microbial colonies. Organic matter also refers to bacteria, viruses, spores, fungi, prions, and other infectious material found in nature.

As used herein, "animal" refers to any organism classified as an animal, which may include, but are not limited, humans, domestic and farm animals, and zoo, sports, or pet animals, such as dogs, cats, cattle, horses, sheep, pigs, goats, rabbits, fish, insects, reptiles, birds etc.

As used herein, "blood cells" in the sense of the present invention are blood cells having or not having a cell nucleus, i.e. nucleated or non-nucleated cells. Non-nucleated red blood cells not having a cell nucleus are e.g. the mature red blood cells as found in the circulation of animals. This invention also relates to nucleated blood cells as e.g. known from avian species. The later ones would meet the criteria for eukaryotic or nucleated cells.

As used herein, a "eukaryotic cell" or a "nucleated cell" in the sense of the present invention is a cell derived from a eukaryotic organism and is still has its cell nucleus. Examples of eukaryotic cells are cells derived from nucleated tissue, nucleated tissue culture cells and nucleated blood cells. In a preferred embodiment the eukaryotic cell is a nucleated blood cell like a thrombocyte, a monocyte, neutrophils, eosinophils or a leukocyte.

As used herein, "cells from lower organisms" may include, but are not limited, bacteria, viruses, fungi, prions, etc. These cells contain genetic material, but they are not eukaryotic cells.

As used herein, the expression "oxidizing agent" refers in chemistry to a substance that has the ability to oxidize other substances—in other words, to cause them to lose electrons. In one sense, an oxidizing agent is a chemical species that undergoes a chemical reaction that removes one or more electrons from another atom. In that sense, it is one component in an oxidation-reduction (redox) reaction. In the second sense, an oxidizing agent is a chemical species that transfers electronegative atoms, usually oxygen, to a substrate. Common oxidizing agents may include, but are not limited, oxygen ($O_2$), superoxide ($O_2^-$), urea, peracetic acid, ozone, peroxides, including hydrogen peroxide and other inorganic peroxides, Fenton's reagents, halogens, such as fluorine and chlorine, nitric acid, nitrate and nitrate compounds, sulfuric acids, including peroxydisulfuric acid and peroxymonosulfuric acid, hypochlorite, chlorite, perchlorite, sodium hypochlorite, chlorate, perchlorate, chromium, chromic and dichromic acids and chromium trioxide, pyridinium chlorochromate, and cerium (IV) compounds such as ceric ammonium nitrate and ceric sulfate. This list is used as an example but is not inclusive of all known oxidizing agents.

As used herein, the expression an "Augmented Oxidizing Agent" (AOA) refers to an oxidizing agent that has been exposed a certain wavelength of radiation to create Electronically Modified Oxygen Derivatives (EMODs). EMODs are generated through a synergistic chemical reaction of oxidizing agents and the radiation. EMODs are chemically reactive chemical species containing oxygen. Examples of EMODs include peroxides, superoxide, hydroxyl radical, and singlet oxygen.

As used herein, the term "radiation" refers in physics to the emission or transmission of energy in the form of waves or particles through space or through a material medium. This includes, but is not limited to: (1) electromagnetic radiation, such as radio waves, microwaves, ultraviolet light, visible light, x-rays, and gamma ($\gamma$) radiation, (2) particle radiation, such as alpha ($\alpha$) radiation, beta ($\beta$) radiation, and neutron radiation (particles of non-zero rest energy), (3) acoustic radiation, such as ultrasound, sound, and seismic waves (dependent on a physical transmission medium), and (4) gravitational radiation, radiation that takes the form of gravitational waves, or ripples in the curvature of spacetime.

The word "radiation" arises from the phenomenon of waves radiating (i.e., traveling outward in all directions) from a source. This aspect leads to a system of measurements and physical units that are applicable to all types of radiation. Because such radiation expands as it passes through space, and as its energy is conserved (in vacuum), the intensity of all types of radiation from a point source follows an inverse-square law in relation to the distance from its source. Like any ideal law, the inverse-square law approximates a measured radiation intensity to the extent that the source approximates a geometric point. Some of the ultraviolet spectrum that begins above energies of 3.1 eV, a wavelength less than 400 nm is non-ionizing, but is still biologically hazardous due to the ability of single photons of this energy to cause electronic excitation in biological molecules, and thus damage them by means of certain reactions. This property gives the ultraviolet spectrum some of the properties of ionizing radiation in biological systems without actual ionization occurring. In contrast, visible light and longer-wavelength electromagnetic radiation, such as infrared, microwaves, and radio waves, consists of photons with too little energy to cause damaging molecular excitation. Light, or visible light, is a very narrow range of electromagnetic radiation of a wavelength that is visible to the human eye, or 380-750 nm which equates to a frequency range of 790 to 400 THz respectively. More broadly, physicists use the term "light" to mean electromagnetic radiation of all wavelengths, whether visible or not.

As used herein, the singular forms "a", "an", and "the" include plural references unless the context clearly dictates otherwise. By way of example, "a red blood cell" means one red blood cell or more than one red blood cell. All numerical values within the detailed descriptions and the claims herein are modified by "about" or "approximately" the indicated value and take into account experimental error and variations that would be expected by a person having ordinary skills in the art.

Reference will now be made in detail to exemplary embodiments of the disclosure.

While the disclosure will be described in conjunction with the exemplary embodiments, one skilled in the art can understand that it is not intended to limit the disclosure to those embodiments. Any combination, devices or methods provided herein can be combined with one or more of any of the other combination, devices and methods provided herein. To the contrary, this invention is intended to cover alternatives, modifications, and equivalents as may be included within the spirit and scope of the disclosure as defined by the appended claims.

In a first exemplary embodiment, the present invention relates to a method of hemolyzing a quantity of blood and suspected or known blood components comprising plasma, TDS, TSS, eukaryotic cells, and other components of blood by application of Augmented Oxidizing Agents (AOA) containing EMODs to the target blood. The EMODs are components involved in the killing response of immune cells in response to microbial invasion. Recent evidence has shown that they play a key role as a messenger in normal cell signal transduction and cell cycling.

These reactive molecules are formed by a number of different mechanisms in nature, but the process as described herein forms them in numbers greater than found in nature. The process described herein also produces EMODs that exist for a longer duration than typically found in nature. Some examples of EMODs are superoxide; hydrogen peroxide; hydroxyl radical; hydroxyl ion; and nitric oxide. These EMODs are generated by exposing Oxidizing Agents to radiation of a certain wavelength, generally between 300 nm and 600 nm, where the interaction of these agents, oxidizing agents and radiation, when combined produce a total effect that is greater than the sum of the effects of the individual agents. This radiation exposure generates EMODs that last longer than typically found in nature by evidence of a residual effect which research has shown as an increased effect that lasts for days, thereby providing an AOA. The expected EMODs' life span when they are found naturally in nature is measured in nanoseconds. Exposing oxidizing agents to radiation produces an AOA having a unique EMOD that exhibits a residual effect demonstrated by its existence for hours, days, weeks and greater extended periods of time. The radiation wavelength of between 300 nm and 600 nm may be produced from a variety of sources such as LEDs, lasers, natural light, electromagnetic radiation, arc lamps and other suitable sources. The list of radiation producing sources is not meant to limit sources to those listed but to serve as an example.

Processing of said target blood with an AOA containing EMODs in solution, which is a result of an oxidizing agent that has been exposed to radiation of certain wavelengths where the interaction of oxidizing agent and radiation, when combined, produce a total effect that is greater than the sum of the effects of these individual components, under conditions appropriate to lyse cell membranes of blood cells and at the same time causing or not causing precipitation of sample constituents depending on need, potentially subjecting the processed sample obtained in the first step to separation into desired components such as liquids and solids.

The below Table 1 shows actual testing results that illustrate the residual effect of Augmented Oxidizing Agents (AOAs) containing EMODs created by methods of present invention. The test substance was a solution of 3% hydrogen peroxide, which was exposed to radiation to form the AOA containing EMODs. The test substance or AOA was applied to target, which included a carrier with a viable bacteria concentration of anaerobic bacteria *Staphylococcus epidermidis* ATCC 12228. The AOA was applied 1 minute, 5 minutes, 10 minutes, 30 minutes, 1 hour, 12 hours, 24 hours, 2, days, 5 days, and 7 days after radiation exposure. After 7 days, AOA was again subjected to radiation for reactivation.

TABLE 1

| Test Microorganism | Test Substance Concentration | Time After Radiation Exposure Substance Applied to Carrier | CFU/carrier | Percent Reduction vs. Parallel Control | $Log_{10}$ Reduction vs. Parallel Control |
|---|---|---|---|---|---|
| S. epidermidis ATCC 12228 | Control | N/A | 6.04E+05 | N/A | N/A |
| | | 1 Minute | 7.00E+04 | 88.42% | 0.94 |
| | | 5 Minute | 7.00E+04 | 88.42% | 0.94 |
| | 3% $H_2O_2$ | 10 Minute | 3.10E+04 | 94.87% | 1.29 |
| | | 30 Minute | 2.80E+04 | 95.37% | 1.33 |
| | | 1 Hour | 7.10E+04 | 88.25% | 0.93 |
| | 12 Hour Control | | 9.20E+04 | N/A | N/A |
| | 3% $H_2O_2$ | 12 Hours | 1.80E+04 | 80.43% | 0.71 |
| | 24 Hour Control | | 1.33E+05 | N/A | N/A |
| | 3% $H_2O_2$ | 24 Hours | 2.10E+04 | 84.21% | 0.80 |
| | 2 Day Control | | 3.00E+05 | N/A | N/A |
| | 3% $H_2O_2$ | 2 Days | 9.00E+04 | 70.00% | 0.52 |
| | 5 Day Control | | 4.50E+04 | N/A | N/A |
| | 3% $H_2O_2$ | 5 Days | 3.29E+03 | 92.69% | 1.14 |
| | 7 Day Control | | 9.80E+04 | N/A | N/A |
| | | 7 Days | 1.50E+04 | 84.69% | 0.82 |
| | 3% $H_2O_2$ | 7 Days with Reactivation | 1.00E+04 | 89.80% | 0.99 |

There are statistical variations but when comparing the increased activation of the AOAs at 1 minute post augmentation with AOA that was augmented 7 days previously, the results are very similar. The Augmented Oxidizing Agent exhibits a pronounced residual effect. This residual effect is evidenced by the antimicrobial effect of the AOAs. The un-augmented oxidizing agents have been shown to exhibit an antimicrobial effect of approximately 30% at a dwell time of 5 minutes. The radiation of between 300 nm and 600 nm has been shown to kill approximately 1% of the microbes that are exposed to it for 5 minutes. The Augmented Oxidizing Agents demonstrate an antimicrobial effect over 100% greater than un-augmented oxidizing agents. This effect provides a concentration of an oxidizing agent with double the antimicrobial effect or a concentration of AOA can be utilized that is 50% or less of the concentration of the un-augmented oxidizing agent and exhibit the same antimicrobial activity.

Another exemplary embodiment of the present invention relates to the use of a solubilizing agent that includes an AOA, which contains EMODs, in the processing of a blood sample for separation and to the use of a processed blood sample obtained by separation so that its components may be discarded or repurposed individual or in subsets. The AOA results from an oxidizing agent exposed to radiation of certain wavelengths, and the interaction of the oxidizing agent and radiation, when combined, produce an AOA having a total effect that is greater than the sum of the effects of the oxidizing agent and radiation. The EMODs may be generated by exposing the oxidizing agent or agents to radiation of certain wavelengths before the oxidizing agent is applied to a target or exposing the oxidizing agent to radiation while the oxidizing agent is applied to a target or applying an oxidizing agent or oxidizing agents to a target then exposing the entire mixture to radiation of certain wavelengths.

The method according to the present invention is performed on a sample or target material in vitro, i.e. not on the human or animal body.

The sample or target material includes organic matter, which pertains to any carbon-based compound that exists in nature. For example, living things are described as organic since they are composed of organic compounds. Examples of organic compounds are carbohydrates, lipids, proteins and nucleic acids. Since they are comprised of carbon-based compounds, they are broken down into smaller, simpler compounds through decomposition and through lysing. Living organisms also excrete or secrete material that is considered an organic material. The organic matter from blood may contain useful substances that contribute a value when separated from the blood, etc and suspected or known to comprise nucleated cells, non-nucleated cells, cell components, microbes and organic matter. This organic matter contains substances that can be repurposed as food sources, as fertilizer, as medicines or and other uses.

An exemplary embodiment of the invention relates to a method comprising the steps of processing a sample or target material that includes organic matter with a membrane solubilizing agent consisting of an oxidizing agent such as oxygen ($O_2$), superoxide ($O_2^-$), urea, peracetic acid, ozone, hydrogen peroxide, other inorganic peroxides, Fenton's reagents, fluorine, chlorine, halogens, nitric acid, nitrate compounds, sulfuric acids, peroxydisulfuric acid, peroxymonosulfuric acid, hypochlorite, chlorite, perchlorite, halogen compounds, sodium hypochlorite, chlorate, perchlorate, chromium, chromic and dichromic acids, chromium trioxide, pyridinium chlorochromate, cerium (IV) compounds such as ceric ammonium nitrate and ceric sulfate and other agents. This list is used as an example but is not inclusive of all oxidizing agents.

The oxidizing agent is exposed to radiation between 300 nm and 600 nm. This creates an Augmented Oxidizing Agent, AOA, that contain more EMODs than similar substances found in nature. These excess EMODs generate a newly discovered residual effect whereby the EMODs last for an extended period of time.

The EMODs are components of the killing response of immune cells to microbial invasion. Recent evidence has shown that they play a key role as a messenger in normal cell signal transduction and cell cycling. These reactive molecules are formed by a number of different mechanisms in nature but the process described in this patent forms them in numbers greater than found in nature. Some examples of EMODs are superoxide; hydrogen peroxide; hydroxyl radical; hydroxyl ion; and nitric oxide thereby lysing cell membranes of blood cells, nucleated cells, non-nucleated cells, cell components, microbes, organic matter and microbial cells. This method results in a product that is free of most if not all microbes, bacteria, viruses, spores, fungi, prions, and other infectious material found in nature, has a lowered TDS and TSS and includes components that can be discarded or repurposed.

For example, blood contains 16 to 18 percent protein solids and dried blood meal is a valuable ingredient in feed for non-ruminant animals because it has a high lysine content. Blood meal is also used as a high-nitrogen fertilizer. In an exemplary embodiment, the present invention relates to a method of lysing a quantity of animal fluids, blood, blood cells, microbes, and organic matter and suspected or known blood components comprised of plasma, TDS, TSS, eukaryotic cells, microbes, bacteria, viruses, spores, fungi, prions, and other infectious material and other passible components of blood by application of AOAs comprising EMODs to a target blood sample. These Augmented Oxidizing Agents comprising the Electronically Modified Oxygen Derivatives are generated by exposing oxidizing agents to radiation of a certain wavelength where the interaction of the oxidizing agents and radiation produce a total effect that is greater than the sum of the effects of the oxidizing agents or radiation alone. This radiation exposure generates EMODs that last longer than typically found in nature by evidence of a residual effect which research has shown as an increased antimicrobial effect that lasts for over 7 days. Processing and lysing of said animal fluids, blood, blood cells, blood sample, microbes, and organic matter with an AOA comprising EMODs provides a total effect that is greater than the sum of the effects of the oxidizing agent or radiation under conditions appropriate to lyse cell membranes of animal fluids, blood, blood cells, microbes and organic matter and at the same time causing or not causing precipitation of sample constituents depending on need, potentially subjecting the processed sample obtained in the first step to separation into desired components such as liquids and solids. EMODs are components of the killing response of immune cells to microbial invasion. Recent evidence has shown that they play a key role as a messenger in normal cell signal transduction and cell cycling. These reactive molecules are formed by a number of different mechanisms in nature, but the process described in this patent forms them in numbers greater than found in nature and creates EMODs that exist for a longer period of time then EMODs naturally found in nature. Some examples of chemicals containing EMODs are superoxide; hydrogen peroxide; hydroxyl radical; hydroxyl ion; and nitric oxide.

It may be desired to inactivate substances found in a sample including blood or other target materials that reduce the effectiveness of AOA with EMODs. This can be done, for example, by adjusting the pH of the sample or target material or by exposing the target material to temperatures that denature the substance or enzyme that reduces the effectiveness of the AOA. The adjustment of the pH or exposure to such temperatures may be carried out before, during, and/or after the sample or target material is contacted or exposed to the AOA. A combination of temperature changes and pH changes may also be used.

During the storage or transport of the blood, blood cells, body fluids, etc., other exogeneous organic matter may be incorporated into the sample. For example, slaughtered animals consist of organic matter, but exogenous organic matter may also be incorporated into samples before being lysed. This exogenous matter may include microbes or microbial colonies that exist in the collected sample either before or after lysing. Some substances contained in a sample of organic material may destroy or reduce the effectiveness of AOA. These substances may contain or consist of enzymes such as catalase. To increase the effectiveness of AOAs, a solution of AOA may be heated to a point where the substance that adversely effects the oxidizing agent is reduced in effectiveness or destroyed. This may also be accomplished by cooling an AOA solution to a point that leaves the substance that adversely effects the AOA reduced in effectiveness or destroyed.

In another exemplary embodiment, the present invention relates to a method of hemolyzing a sample known or suspected to comprise blood and blood cells and/or suspected or known to comprise eukaryotic cells, blood components, or blood products, the method comprising the steps of a) processing said sample with a solubilizing agent consisting of an oxidizing agent that has been exposed to certain wavelengths of radiation, when combined produce a total effect that is greater than the sum of the effects of the oxidizing agent and radiation (i.e. an AOA with EMODs), under conditions appropriate to lyse cell membranes of blood cells and at the same time causing or not causing precipitation of constituents, b) subjecting the processed sample obtained in step (a) to separation, and c) qualifying and quantifying the analyte.

The advantageous properties of hemolysis as demonstrated in the present invention have been established by using blood samples, i.e. of processing a sample with a solubilizing agent according to the present invention under conditions appropriate to lyse cell membranes of blood cells, microbial cells, TDS, TSS and other components in blood and at the same time not to cause or to cause, based on the desired outcome, precipitation of sample constituents. However, other liquid samples may be used and processed in a similar way. A sample according to the present invention may be any sample as investigated in processing routine, like urine, cerebrospinal fluid, plasma, blood or other parts of animals.

In other exemplary embodiment, a sample subjected to a differential hemolysis with an appropriate solubilizing agent comprises blood cells and may comprise or comprises nucleated cells or non-nucleated cells. Alternatively, the liquid sample may comprise both blood cells and nucleated cells and non-nucleated cells. The sample according to the present invention may also be blood. As will be appreciated a whole blood sample contains both red blood cells without nuclei as well as nucleated blood cells. These nucleated and non-nucleated cells make up a significant portion of the TDS and TSS.

The blood sample may be processed directly, i.e. directly after collecting in the method according to the present invention or indirectly, i.e. after a period of time. The blood sample may or may not be treated at all before it is subjected to the hemolysis according to the present invention. This treatment may consist of coagulation, anticoagulation, addition of a flocculant, filtering, cooling, heating, the application of sonic or ultrasonic energy, ultraviolet or other light therapy, antimicrobial agents and other commercially available processes that may apply. Also, the blood may be collected and treated or not treated with an appropriate anti-coagulant to yield an anti-coagulated blood sample, before it is hemolysed. Well-known anti-coagulants frequently used may consist of heparin, citrate and EDTA but not limited too.

In an exemplary method according to the present invention the blood sample is treated with solubilizing agent consisting of an AOA, which has been prepared from an oxidizing agent that has been exposed to radiation between 300 nm and 600 nm. This combination oxidizing agent and radiation generates an AOA with EMODs that exhibit antimicrobial properties, lysing properties and residual effects. This list of properties is not meant as all inclusive but instead is meant to illustrate some of the effects of the AOAs. The EMODs work in such a manner that two requirements are met: a) if blood cells are present, the membranes of blood cells are disrupted and b) at the same time no precipitation of sample constituents is caused unless precipitation is desired. This process is termed hemolysis. In case the method is practiced on blood, a processed sample is obtained containing lysed blood cells but at the same no precipitate is formed unless it is desired. The solubilizing agent consists of an oxidizing agent that has been exposed to wavelengths of radiation between 300 nm and 600 nm. That is, the solubilizing agent consists of an AOA. This exposure can be before the AOA is applied to a target, while the AOA is applied to a target or after the AOA is applied to a target or a combination of the above applications of radiation.

The membrane solubilizing agent consisting of AOAs according to the present invention will bring about the lysis of the cells and constituents of cells present in a sample. These constituents may consist of any carbon-based compound that exists in nature or exist in living things. Examples of associated compounds are carbohydrates, lipids, proteins and nucleic acids. Since they are comprised of carbon-based compounds, they are broken down into smaller, simpler compounds through decomposition and through lysing. Living organisms also excrete or secrete material that is considered an organic material. The organic matter from blood may contain useful substances that contribute a value when separated from the blood. These useful substances can be utilized as feed for animals and fertilizer for plants among other uses. Further preferred the reagent for hemolysis will bring about the lysis of microbial cells and their constituents in the sample. The term microbes is used to represent some or all of the following list but the list is used as an example but not meant to be all inclusive: bacteria, viruses, fungi, spores, prions and other known or yet unknown disease causing organisms.

For example, in an exemplary embodiment, the present invention relates to method for lysing a sample or target material comprising animal fluids, blood, blood cells, nucleated blood cells, non-nucleated blood cells, cell components, microbes, bacteria, viruses, spores, fungi, prions, and/or organic matter to reduce or eliminate constituents selected from the group consisting of total dissolved solids (TDS), total suspended solids (TSS), minerals, proteins, microbes, bacteria, viruses, spores, fungi, and prions and combinations thereof so that the constituents can be separated from the target material. Steps in the method may include, for example, creating an AOA by exposing at least one oxidizing agent to radiation between 300 nm and 600 nm, the AOA containing EMODS at a greater concentration then non-irradiated oxidizing agents. The target material is subjected to the AOA, e.g. by applying the AOA onto target material. The AOA may be created prior to applying to the target material, during or while the oxidizing agent is applied to the target material, and/or after the oxidizing agent is applied to the target material. The EMODs of the AOA lyse the target material by destroying cell walls, cell components, genetic material and other organic matter. Optionally, the target material may be subjected to cooling and/or heating before, during and/or after exposure to the AOA to inactivate substances, and/or pH adjustment before, during and/or after exposure to the AOA. Also, additional components, such as a flocculant, may be mixed with the target material before, during, and/or exposure to the AOA to facilitate separation. After the target material has been exposed to the AOA, e.g. by its application to the target material, separation may be performed by a centrifuge, a decanter, or a filter thereafter so that the resulting solid and/or liquid components may be collected.

Without wanting to be bound to the following theory one may assume that the advantageous balance found and established within the framework of the present invention, at which the membrane of a blood cell is disrupted but at which at the same time no precipitation of sample constituents is caused is essential for overcoming at least some of the problems known from the art. By applying a suitable membrane solubilizing agent, AOA, under appropriate conditions the integrity of the cellular membrane that is e.g. essential for shielding the contents of a blood cell from the blood plasma is lost. The content of the erythrocytes (e.g. hemoglobin but also some analytes of interest) is released into the surrounding liquid. At the same time no precipitation of sample constituents is caused but may be allowed as desired.

As the skilled artisan will appreciate, sample constituents that might be a constituent in a latter analysis may especially be DNA and de-natured proteins, respectively. The integrity of blood cells can for example be assessed by appropriate life stains. In a preferred embodiment according to the present invention trypan blue is used in order to assess the integrity of a red blood cell, membrane Intact red blood cells do not accumulate trypan blue, whereas a red blood cell with a disrupted membrane does stain with trypan blue. The membrane integrity of a red blood cell is easily assessed under the microscope after staining a sample with trypan blue. The percentage of disrupted red blood cells is calculated by counting intact red blood cells before and after the treatment, by then dividing the first number by the latter number and by then multiplying this value by Red blood cells that are solubilized are referred to as lysed red blood cells or as lysed erythrocytes. The appropriate treatment will be adequate to lyse a blood cell, but at the same time it may or may not cause precipitation of sample constituents. It is expected that the appropriate hemolysis treatment in a method according to the present invention will also affect the outer membranes of eukaryotic cells. The hemolysis reagent and the conditions for hemolysis used may or may not leave the nuclear membrane and thus the nuclei macroscopically intact or at least DNA will not be set free from its surrounding and DNA-stabilizing nuclear proteins. As indicated above, the conditions used in this method of hemolysis according to the present invention can easily be assessed visually. If a blood sample is incubated with an appropriate reagent for hemolysis the minimal concentration required to hemolyze red blood cells can be recognized as the concentration rendering the turbid blood sample transparent or clear.

In another exemplary embodiment according to the present invention a blood sample derived from an animal or a sample of blood derived from an animal will be subjected to the treatment with a membrane solubilizing agent as described in the present invention may be accomplished without any additional step like filtration, precipitation or centrifugation or those steps may be used. In a preferred embodiment therefore the present invention relates to method of hemolyzing a sample of blood, comprising the steps of processing the sample with a membrane solubilizing agent under conditions appropriate to disrupt the membrane of said animal fluids, blood, blood cells, microbes, including bacteria, viruses, fungi, spores, prions and other known or yet unknown disease causing organisms, but not to destroy the nuclei of eukaryotic cells unless desired.

EQUIVALENTS

The foregoing description illustrate the principles, exemplary embodiments, and modes of operation of the invention. However, the invention should not be construed as being limited to the particular exemplary embodiments discussed above. Additional variations of the exemplary embodiments discussed above will be appreciated by those skilled in the art. Using no more than routine experimentation, one skilled in the art will recognize or be able to ascertain, many equivalents to the specific embodiments and methods described herein. Such equivalents are intended to be encompassed by the scope of the following claims.

Therefore, the above-described exemplary embodiments should be regarded as illustrative rather than restrictive. Accordingly, it should be appreciated that variations to those exemplary embodiments can be made by those skilled in the art without departing from the scope of the invention as defined by the following claims. For example, the relative quantities of the ingredients may be varied to optimize the desired effects, additional ingredients may be added, and/or similar ingredients may be substituted for one or more of the ingredients described. Additional advantageous features and functionalities associated with the methods, combinations and devices of the present disclosure will be apparent from the appended claims.

What is claimed is:

1. A method for lysing a target material comprising animal fluids and/or blood to reduce or eliminate constituents selected from the group consisting of total dissolved solids (TDS), total suspended solids (TSS), minerals, proteins, microbes and combinations thereof in a target material so that the constituents can be separated from the target material, the method comprising:
   inactivating enzymes in the target material by heating;
   creating an Augmented Oxidizing Agent(AOA), by exposing at least one oxidizing agent to radiation between 300 nm and 600 nm, the AOA contains Electronically Modified Oxygen Derivatives (EMODs) at a greater concentration than in said at least one oxidizing agent prior to exposure to said radiation,
   subjecting the AOA to the target material with inactivated enzymes, the EMODs of the AOA lysing the target material by destroying cell walls, cell components, genetic material and/or other organic matter in the target material, and
   separating from the lysed target material said constituents selected from the group consisting of TDS, TSS, minerals, proteins, microbes and combinations thereof.

2. The method of claim 1, wherein the separation is performed by a centrifuge, a decanter, or a filter.

3. The method of claim 1, wherein separated solid components are collected.

4. The method of claim 1, wherein separated liquid components are collected.

5. The method of claim 1, wherein the AOA is created by exposing the oxidizing agent to the radiation before the target material is subjected to the AOA.

6. The method of claim 1, further comprising applying the oxidizing agent to the target material, wherein the AOA is created by exposing the oxidizing agent to the radiation while the oxidizing agent is applied to the target material.

7. The method of claim 1, further comprising applying the oxidizing agent to the target material, wherein the AOA is created by exposing the oxidizing agent to the radiation after the oxidizing agent is applied to the target material.

8. The method of claim 1, wherein the AOA is created during at least one time selected from the group consisting of before subjecting the target material is subjected to the AOA, while the oxidizing agent is applied to the target material, and after the oxidizing agent is applied to the target material.

9. The method of claim 1, wherein the target material is heated or cooled before, during or after lysing by the AOA.

10. The method of claim 1, wherein the oxidizing agent is heated or cooled before after or during exposure to the radiation to create the AOA.

11. The method of claim 1, wherein the AOA created by exposing the oxidizing agent to the radiation exhibits a residual effect where the EMODs exist for a time that is longer than nano-seconds.

12. The method of claim 1, wherein the target material to be lysed is cooled to inactivate substances before subjecting the target material to the AOA.

13. The method of claim 1, wherein the target material to be lysed is heated and cooled to inactivate substances before subjecting the target material to the AOA.

14. The method of claim 1, wherein the target material to be lysed has its pH adjusted before, during, and/or after subjecting the target material to the AOA.

15. The method of claim 1, further comprising adding a flocculent to target material before, during and/or after subjecting the target material to AOA.

16. A method for lysing a target material selected from the group consisting of an animal fluid, blood, and a sample comprising blood cells to reduce or eliminate constituents in the target material selected from the group consisting of total dissolved solids (TDS), total suspended solids (TSS), minerals, proteins, microbes and combinations thereof, the method comprising:
creating an Augmented Oxidizing Agent (AOA), by exposing at least one oxidizing agent to radiation between 300 nm and 600 nm, the AOA contains Electronically Modified Oxygen Derivatives (EMODs) at a greater concentration than in said at least one oxidizing agent prior to exposure to radiation,
subjecting the AOA to the garget material, the EMODs of the AOA lysing the target material by destroying cell walls, cell components, genetic material and/or other organic matter in the target material,
separating constituents selected from the group consisting of total dissolved solids (TDS), total suspended solids (TSS), minerals, proteins, microbes and combinations thereof from the lysed target material,
further comprising denaturing enzymes in the target material by heating and/or adjusting pH before, during, and/or after the target material is subjected to the AOA.

* * * * *